US00PP37737P2

(12) United States Plant Patent
Peterse

(10) Patent No.: US PP37,737 P2
(45) Date of Patent: Oct. 6, 2026

(54) ***UGNI* PLANT NAMED 'PI16'**

(50) Latin Name: *Ugni molinae*
Varietal Denomination: PI16

(71) Applicant: Viveros Hijuelas S.A., Hijuelas (CL)

(72) Inventor: Arie Peterse, Noordwijk (NL)

(73) Assignee: VIVEROS HIJUELAS S.A., Hijuelas (CL)

( * ) Notice: Subject to any disclaimer, the term of this patent is extended or adjusted under 35 U.S.C. 154(b) by 0 days.

(21) Appl. No.: 19/444,159

(22) Filed: Jan. 8, 2026

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./156, 226
See application file for complete search history.

*Primary Examiner* — Susan McCormick Ewoldt
(74) *Attorney, Agent, or Firm* — Penny J. Aguirre

(57) ABSTRACT

A new cultivar of *Ugni* plant named 'PI16' that is characterized by its dense and compact plant habit, its young foliage that is greyed-orange to greyed-red in color, its mature foliage that is healthy and dark green in color, its mature foliage that is healthy and dark green in color, and its desirable fruit that are red in color and edible with a pleasant taste.

4 Drawing Sheets

Botanical classification: *Ugni molinae.*
Variety denomination: 'PI16'.

CROSS REFERENCE TO A RELATED APPLICATION

This application is related to a European plant breeders' rights application filed on Apr. 2, 2024, application No. 2024/0776. All information for the plant breeders' rights application was received directly from the Inventor.

BACKGROUND OF THE INVENTION

The present invention relates to a new and distinct cultivar of *Ugni molinae* and will be referred to hereafter by its cultivar name 'PI16'. 'PI16' is a new cultivar of Chilean guava; semi-evergreen shrub grown for use as a landscape plant and its edible fruit for home gardeners.

The new cultivar was derived from a controlled breeding program conducted by the Inventor in Hijuelas, provincia de Quillota, Chile. The overall purpose of the breeding program was to develop a new cultivar of *Ugni* plants with good ornamental value and edible fruits.

The new cultivar arose from open pollination of an unnamed and unpatented proprietary selection of *Ugni molinae* in Hijuelas, provincia de Quillota, Chile in summer of 2013. The male parent is therefore unknown. 30 plants of the resulting seedlings were selected for further evaluation in Kaatsheuvel, The Netherlands where the Inventor selected 'PI16' as a single unique plant amongst the seedlings in September of 2020.

Asexual propagation of the new cultivar was first accomplished by the Inventor by stem cuttings in September of 2020 in Kaatsheuvel, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PI16' as a unique cultivar of *Ugni.*

1. 'PI16' exhibits a dense and compact plant habit.
2. 'PI16' exhibits young foliage that is greyed-orange to greyed-red in color.
3. 'PI16' exhibits mature foliage that is healthy and dark green in color.
4. 'PI16' exhibits desirable fruit that are red in color and edible with a pleasant taste.

The female parent of 'PI16' differs from 'PI16' in having a less compact plant habit and less branching. 'PI16' can be most closely compared to the *Ugni molinae* cultivars 'Elite' (not patented) and 'Villarica Strawberry' (not patented). Both 'Elite' and 'Villarica Strawberry' are similar to 'PI16' in plant shape. 'Elite' differs from 'PI16' in having leaves that are narrower and lighter green in color, darker red colored fruits, and a less floriferous blooming habit with less fruit production. 'Villarica Strawberry' differs from 'PI16' in having leaves that are narrower and lighter green in color and flowers that are larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Garden Crossings, Facebook, Plantarium, Spring Meadow Nursery, Proven Winners, KVBC, Plantago, Nezabravkaflowers, Aiph, Floral Daily, Hortweek, and Plantarium Groen Direkt.

BRIEF DESCRIPTION OF THE DRAWINGS

The accompanying color photographs illustrate the overall appearance and distinct characteristics of the new *Ugni*. The photographs were taken of a 3-year-old plant of 'PI16' as grown outdoors in a 29-cm container in Lochristi, Belgium.

The photograph in FIG. 1 provides a side view of 'PI16' in bloom.

Figure 1:
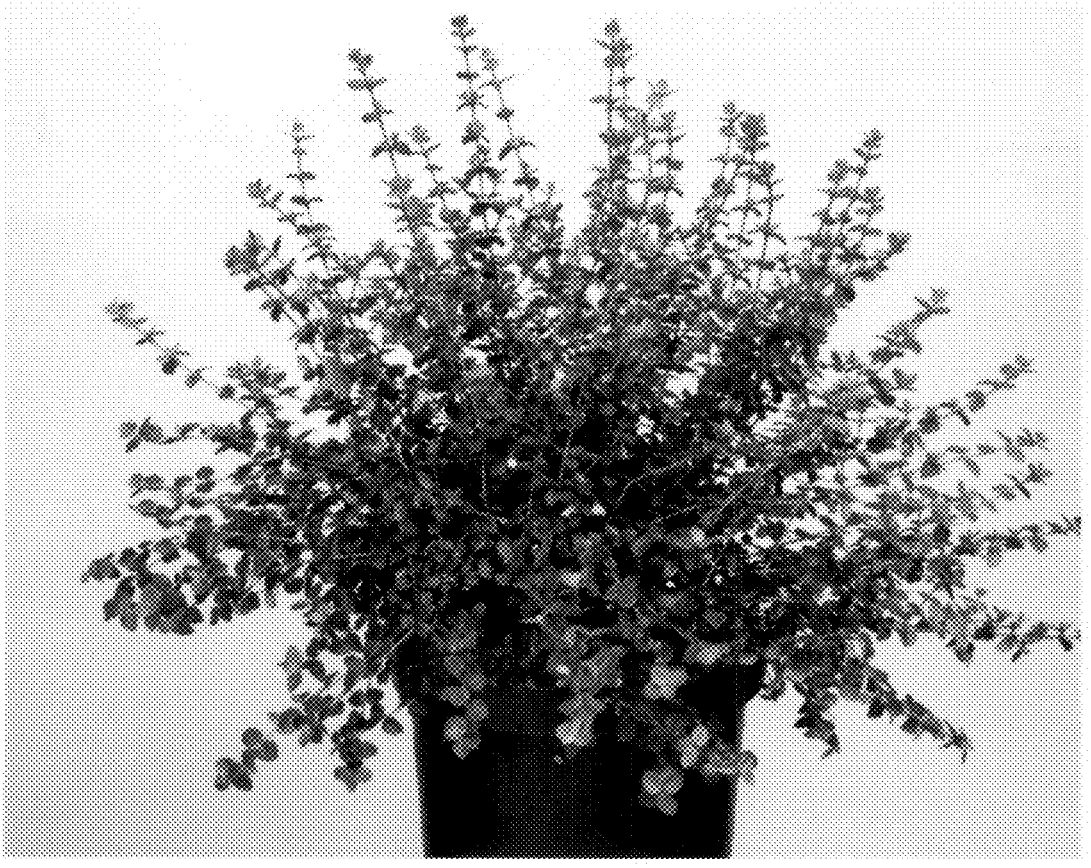
Figure 2:
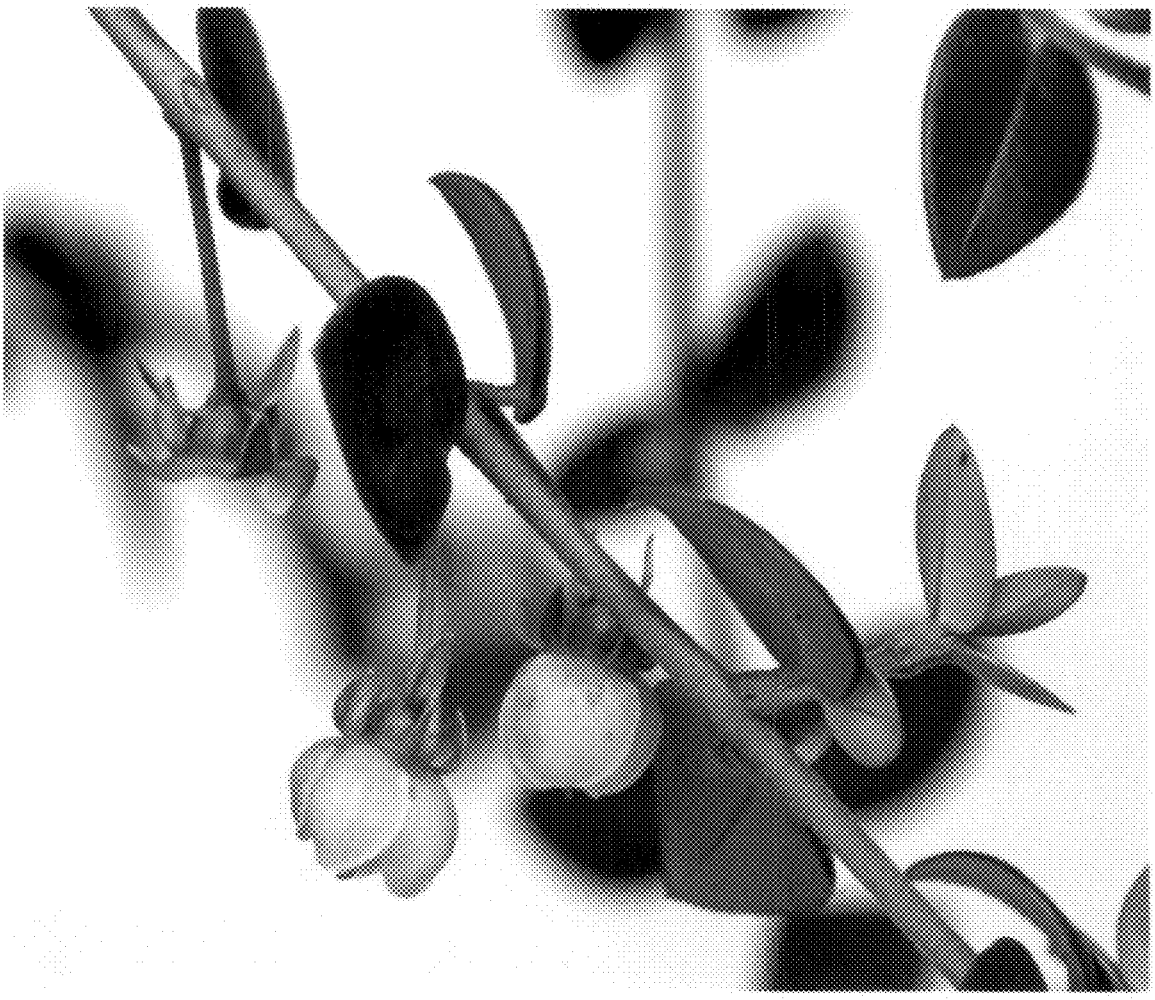

The photograph in FIG. 2 provides a close-up view of the flowers of 'PI16'.

Figure 3:
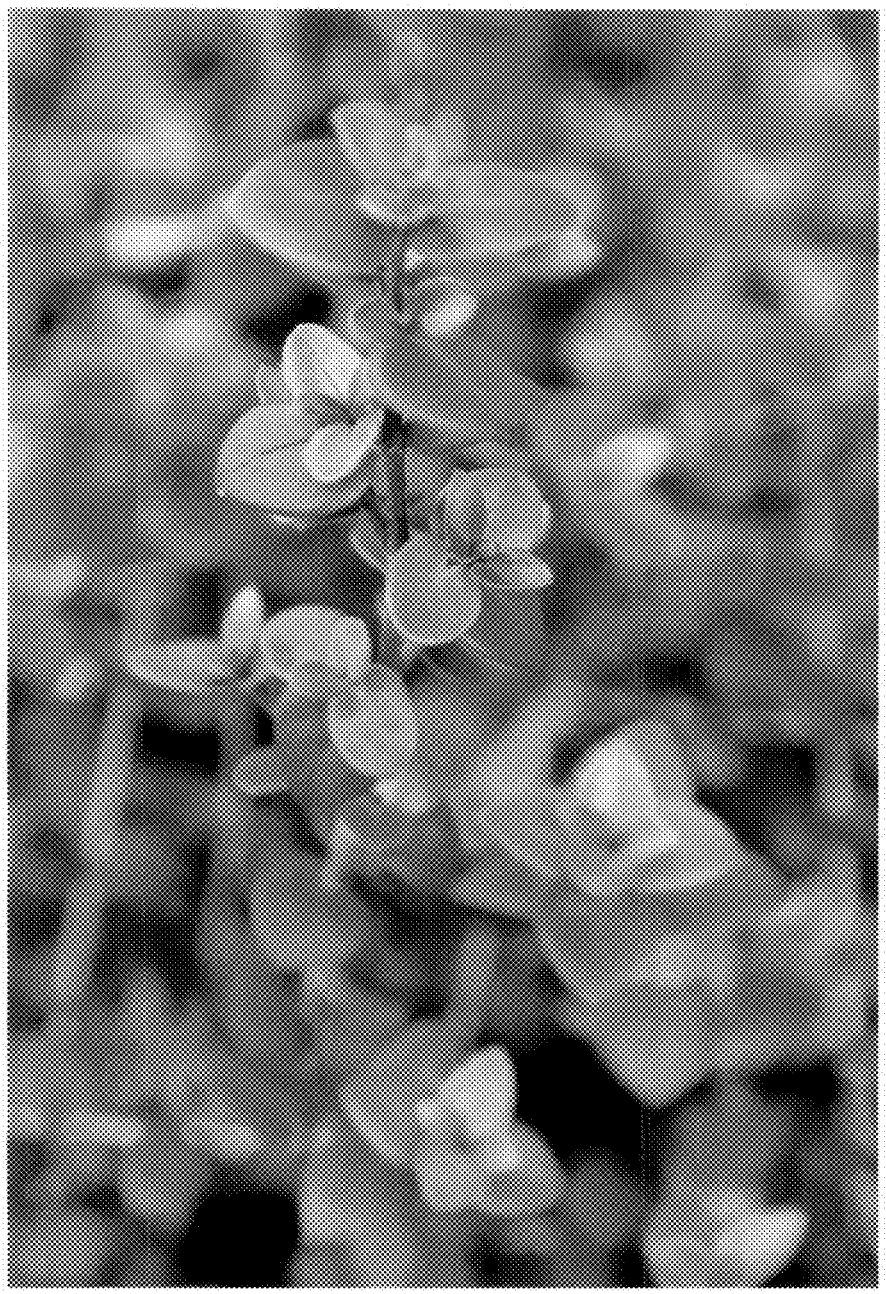

The photograph in FIG. 3 provides a close-up view of the young foliage of 'PI16'.

Figure 4:
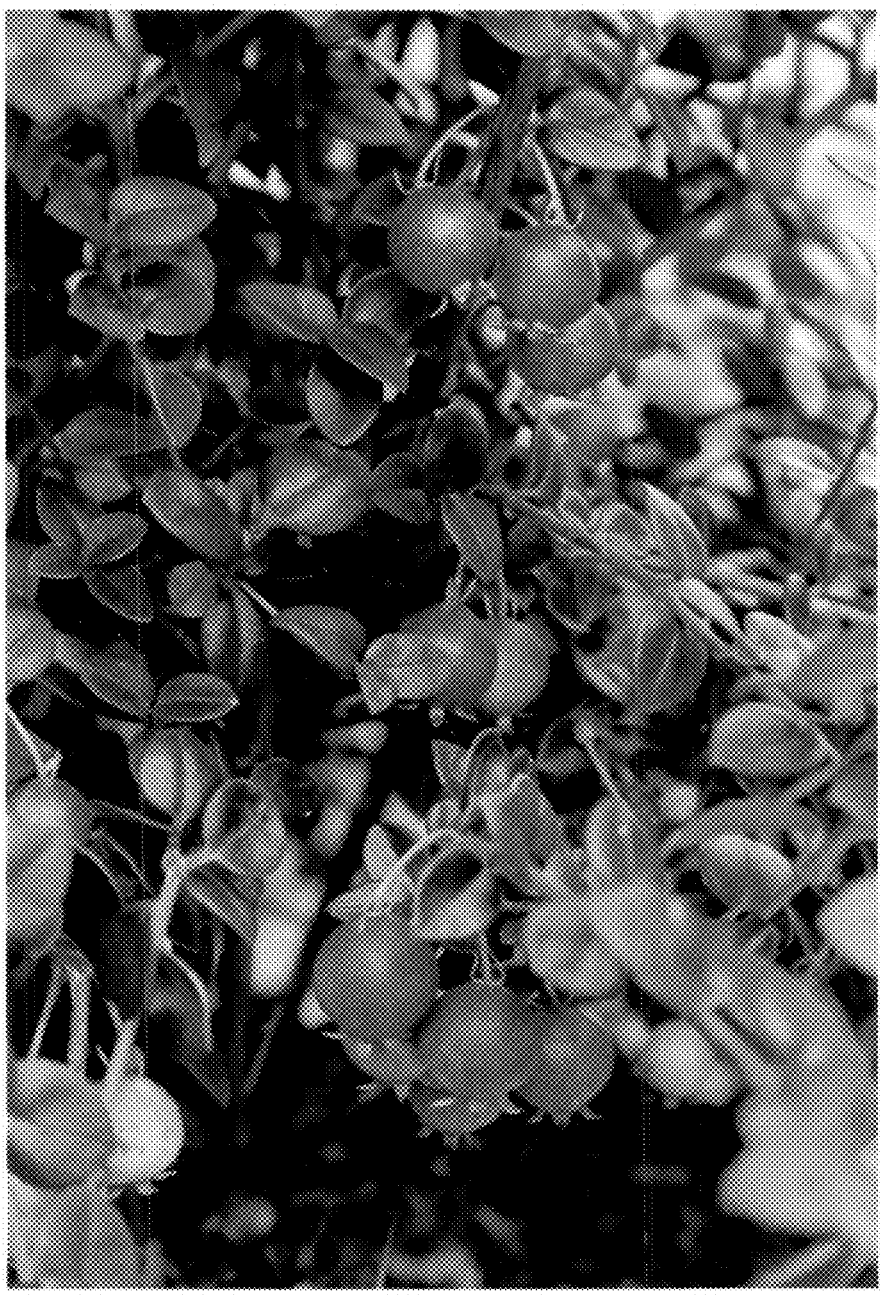

The photograph in FIG. 4 provides a close-up view of the mature foliage and fruit of 'PI16'.

The colors in the photographs may differ slightly from the color values cited in the detailed botanical description, which accurately describe the colors of the new *Ugni*.

DETAILED BOTANICAL DESCRIPTION

The following is a detailed description of the new cultivar as observed for plants 3 years in age as grown outdoors in 29-cm containers in Lochristi, Belgum. The phenotype of the new cultivar may vary with variations in environmental, climatic, and cultural conditions, as it has not been tested under all possible environmental conditions. The color determination is in accordance with the $6^{th}$ edition, 2019 (reprint of 2015) Colour Chart of The Royal Horticultural Society, London, England, except where general color terms of ordinary dictionary significance are used.

General description:

*Blooming period*.—June into August in Chile.

*Plant type*.—Semi-evergreen shrub.

*Plant habit*.—Compact and dense, globular.

*Height and spread*.—An average of 46 cm in height, 73 cm in spread as a 3-year-old plant grown in a container, reaches an average of 1.2 m in height and 90 cm in spread as a mature plant in the landscape.

*Hardiness*.—At least in U.S.D.A. Zones 8 to 11.

*Diseases and pests*.—No resistance or susceptibility to diseases or pest has been observed.

*Root description*.—Fibrous and fine.

*Propagation*.—Vegetative stem cuttings.

*Root development*.—In Chile: time required for root initiation; between 14 days to 3 weeks (depending on growing temperature), time required to produce a fully rooted cutting; 2 to 2.5 months.

Branch description:

*Shape*.—Round.

*Branch color*.—Young; 146B and 146C, mature; 180A with lower surface 173D, bark; N199C and 200D.

*Branch size*.—Average of 30.6 cm in length, 2 mm in diameter.

*Branch surface*.—Glabrous, slightly glossy, stems are moderately pubescent with very short tomentose hairs 0.2 mm in length and too small to measure color.

*Internode length*.—Average of 2.3 cm.

*Branching*.—Densely branched, main branches 45° to soil level, lateral branches 55° to main branches, 18 main branches, 4 lateral branches per main branch.

Foliage description:

*Leaf shape*.—Cordate.

*Leaf division*.—Simple.

*Leaf base*.—Cordate.

*Leaf apex*.—Acute.

*Leaf fragrance*.—When rubbed produces a sweet and pleasant fragrance.

*Leaf venation*.—Pinnate, upper surface 146A, lower surface 148A.

*Leaf margins*.—Entire.

*Leaf arrangement*.—Opposite.

*Leaf aspect*.—Slightly to moderately convex.

*Leaf attachment*.—Petiolate.

*Leaf surface*.—Both surfaces smooth and glabrous, upper surface slightly glossy, lower surface matte to very slightly.

*Leaf size*.—An average of 1.7 cm in length, an average of 1.4 cm in width.

*Leaf color*.—Young upper surface; 146C, strongly tinged N170A and 178B, younger lower surface; 193A, tinged at the margins 172A, mature upper surface; a blend of 139A and 147A, mature lower surface; a blend of 143C and 144A.

*Petioles*.—Average of 3.5 mm in length, 1 mm in diameter, smooth and glabrous, upper surface matte, lower surface moderately glossy, sparse pubescence on the margins 0.3 mm in length, to sparse to measure color, color; upper surface 146D, tinged 182C, lower surface 152C to 152D.

Inflorescence description:

*Inflorescence type*.—Solitary flowers.

*Flower buds*.—Broadly obovate in shape, surface is matte, smooth, and glabrous, 9 mm in length, 7 mm in diameter, color; a blend of N155A to 155B, immature ovary 177C.

*Flower fragrance*.—Sweet fragrance.

*Flower quantity*.—Average of 140 per plant.

*Flower aspect*.—Drooping.

*Flower lastingness*.—About 5 days.

*Flower size*.—Average of 1 cm in diameter and depth.

*Petals*.—4 to 5, orbicular to concave in shape, rotate, 1 whorl, un-fused, both surfaces smooth, glabrous, very slightly glossy, entire margin, broadly cuneate base, obtuse apex, 7 mm in length and width, color; upper surface when opening and fully open 158D, veins 155D, lower surface when opening and fully open 159C and slightly suffused with 146C, veins 159A and 159B fading upper surface 158C, fading lower surface 159A and 159B.

*Calyx*.—Rotate, 3.5 mm in length, 9 mm in diameter.

*Sepals*.—5, 1 whorl, 4 mm in length, 1.75 mm in width, ovate in shape, acute tip, base is fused and broadly cuneate, entire margins, surfaces smooth, glabrous, moderately glossy, color; when opening upper surface 143B, when opening lower surface 146C, fully open upper surface 144A, fully open lower surface 146A.

*Peduncles*.—An average of 1.5 cm in length and 1 mm in width, held in a 80° angle to lateral branch, color; 146A, surface is smooth and very sparsely covered with very short pubescent hairs 0.1 mm in length, too small to measure color.

*Pedicels*.—None, flowers solitary on peduncles.

Reproductive organs:

*Gynoecium*.—Pistils; 1, 6 mm in length, styles; 5.8 mm in length, 182D in color with base N170D, stigmas;

club-shaped, 2 mm in length and diameter, 182C in color, ovary; 176D in color with tip 161C.

*Androecium*.—Stamens; 40, filaments; 2 mm in length, 63A to 63B in color, anthers; dorsifixed and elliptic in shape, 1 mm in length, 0.5 mm in width, 155A in color, pollen; moderate in quantity, 158D in color.

*Fertility*.—Self-fertile.

*Fruit*.—Use: fresh fruit for home gardeners, average of 150 per plant, 1.5 cm in length, 1.35 cm in diameter, surface is smooth, glabrous, very slightly glossy, taste; sweet, somewhat grape-like, pleasant, color; 46A, shady side a blend of 145D and 150D, ripening; 45 days, keeping quality; 2 months.

*Seeds*.—Average of 25 per fruit, 3 mm in length, 1 mm in diameter, surface is smooth and glabrous, 164B in color.

It is claimed:

1. A new and distinct cultivar of *Ugni* plant named 'PI16' as herein illustrated and described.

* * * * *